United States Patent [19]

Gornowicz et al.

[11] Patent Number: 4,705,878
[45] Date of Patent: Nov. 10, 1987

[54] METHOD FOR PREPARING AMINOHYDROCARBYL-SUBSTITUTED KETOXIMOSILANES

[75] Inventors: Gerald A. Gornowicz; Chi-Long Lee, both of Midland, Mich.

[73] Assignee: Dow Corning Corporation, Midland, Mich.

[21] Appl. No.: 18,675

[22] Filed: Feb. 25, 1987

[51] Int. Cl.$^4$ ............................................... C07F 7/08
[52] U.S. Cl. ...................................................... 556/422
[58] Field of Search ......................................... 556/422

[56] References Cited

U.S. PATENT DOCUMENTS

| | | | |
|---|---|---|---|
| 2,672,473 | 3/1954 | Sommer | 556/422 |
| 3,146,250 | 8/1964 | Speier | 260/448.2 |
| 3,189,576 | 6/1965 | Sweet | 260/46.5 |
| 3,674,738 | 7/1972 | Nitzsche et al. | 556/422 X |
| 3,697,568 | 10/1972 | Boissieras et al. | 556/422 |
| 4,126,630 | 11/1978 | Müller et al. | 556/422 |

FOREIGN PATENT DOCUMENTS 57-16893  1/1982  Japan .................................... 556/422

*Primary Examiner*—Paul F. Shaver
*Attorney, Agent, or Firm*—Robert Spector

[57] ABSTRACT

In accordance with the present method a ketoximoaminoalkylsilane is prepared by reacting a ketoxime of the formula RR'C=NOH with a silane of the formula

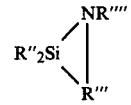

where R and R' represent monovalent hydrocarbon radicals, each of the two substituents represented by R" is, individually, a monovalent hydrocarbon radical, a monovalent fluorinated hydrocarbon radical or an alkoxy radical, R"" represents a monovalent hydrocarbon radical or a hydrogen atom, and R'" represents an alkylene radical containing from 3 to 6 carbon atoms.

4 Claims, No Drawings

METHOD FOR PREPARING AMINOHYDROCARBYL-SUBSTITUTED KETOXIMOSILANES

BACKGROUND OF THE INVENTION

1. Field of the Invention

This invention pertains to a method for preparing silanes. More particularly, this invention pertains to a method for preparing ketoximosilanes containing a silicon bonded aminoalkyl radical.

2. Description of the Prior Art

Silanes containing two or more ketoximo groups bonded to silicon are known in the art. U.S. Pat. No. 3,189,576, which issued to Sweet on June 15, 1965 teaches preparing silanes corresponding to the formula $$(X=NO)_a SiR_{4-a}$$

by reacting a ketoxime of the formula X=NOH with a chlorosilane of the formula $Cl_a SiR_{4-a}$ in the presence of an acid acceptor. The number of moles of ketoxime is at least equal to the number of moles of chlorine present in the silane. In these formulae X= represents $R'_2C=$ or $R''C=$, where R' represents a monovalent hydrocarbon radical or a monovalent halogenated hydrocarbon radical. R is selected from the group consisting of R', cyanoalkyl radicals and the hydrogen atom, R" represents a divalent hydrocarbon radical or a divalent halogenated hydrocarbon radical and a is 1, 2, 3, or 4.

The ketoximosilanes described by Sweet are useful curing agents for one-part moisture curable polyorganosiloxane compositions.

Japanese examined application No. 4837/85, which issued on Feb. 6, 1985, describes a method for preparing ketoximosilanes of the formula $R_a Si(NR'_2)_b(ON=X-)_{4-a-b}$ by the reaction of an alkylaminosilane of the general formula $R_a Si(NR'_2)_{4-a}$ with a ketoxime of the formula X=NOH, where R represents an optionally substituted monofunctional aliphatic, alicyclic or aromatic hydrocarbon radical, R' is R or hydrogen, X is as defined hereinabove for the compounds of the aforementioned Sweet patent, a is 0 or 1, b is 0, 1, 2, or 3, and the sum of a and b is at most 3.

The silicon-nitrogen bond of the ketoximosilanes disclosed in the aforementioned Japanese patent publication would be expected to be unstable due to the relative ease with which a silicon-nitrogen bond can be hydrolyzed.

For some end use applications it would be desirable to have a ketoximosilane containing a primary or secondary amino group that is bonded to silicon through carbon rather than through nitrogen as in the compounds of the aforementioned Japanese patent publication. The amino group provides the means to incorporate a ketoximosilyl group into organic polymers and silicone/organic copolymers containing amine-reactive groups such as isocyanate. The resultant polymers would cure in the presence of atmospheric moisture.

An objective of this invention is to provide a method for preparing ketoximosilanes containing a primary or secondary amino group that is bonded to the silicon atom of the silane by means of a carbon atom.

SUMMARY OF THE INVENTION

In accordance with the present method a ketoximoaminoalkylsilane of the formula (RR'C=NO)R"$_2$SiR'''NR''''H is prepared by reacting ketoxime of the formula RR'C=NOH with a silane of the formula

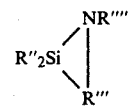

where R and R' represent identical or different monovalent hydrocarbon radicals, the two R" substituents individually represent a monovalent hydrocarbon radical, a monovalent fluorinated hydrocarbon radical, or an alkoxy radical, R"" represents a monovalent hydrocarbon radical or a hydrogen atom, and R''' represents an alkylene radical containing from 3 to 6 carbon atoms.

DETAILED DESCRIPTION OF THE INVENTION

This invention provides a method for preparing an organosilane represented by the formula (RR'C=NO)R"$_2$SiR'''NR''''H, where R and R' represent identical or different monovalent hydrocarbon radicals, each of the two R" substituents individually represents a monovalent hydrocarbon radical, a fluorinated monovalent hydrocarbon radical or an alkoxy group, R''' represents an alkylene radical containing from 3 to 6 carbon atoms, and R"" represents a monovalent hydrocarbon radical or a hydrogen atom, said method comprising the steps of (1) reacting under a substantially anhydrous, inert atmosphere and at a temperature of from 30 to 100 degrees C. a ketoxime of the formula RR'C=NOH and an organosilicon compound of the formula

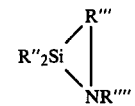

for a sufficient time to form said organosilane, and (2) isolating said organosilane from the reaction mixture.

In accordance with the present method a ketoxime is reacted with a cyclic silylamine. The cyclic portion of the molecule includes the nitrogen and silicon atoms in addition to from 3 to 6 carbon atoms.

The silylamine represented by formula I

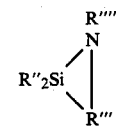

The present method is characterized by displacement of the silicon bonded nitrogen atom in the initial silylamine by the oxygen atom of the ketoxime. The reaction will sometimes be exothermic, however to ensure completeness of the reaction and maximize yields the reaction mixture should be heated at a temperature of from about 40 to about 100 degrees C. for a period of from 30 minutes to several hours, depending on the amounts of reactants used.

Cyclic silylamines corresponding to formula I are described in U.S. Pat. No. 3,146,250, which issued to Speier on Aug. 25, 1964. These silylamines are prepared by reacting a haloalkylhalosilane of the formula R"$_2$Si(R"'X)X where the two substituents represented by X are chlorine, bromine or iodine, with a stoichiometric excess of a primary amine of the formula H$_2$NR"". The reaction is preferably conducted in the presence of a basic material such as a tertiary amine to react with the hydrogen halide generated as a by-product of the reaction.

Representative primary amines include methylamine, ethylamine, n-propylamine, n-butylamine, n-octylamine, aniline and benzylamine. The amine is reacted with a silane containing a silicon bonded chlorine, bromine or iodine atom and a second chlorine, bromine or iodine atom that is part of a silicon bonded monohaloalkyl radical wherein the halogen atom is separated from the silicon atom by an acyclic series of from 3 to 6 carbon atoms. The two remaining substituents on silicon, represented by R" in the foregoing formulae, can be monovalent hydrocarbon radicals, such as methyl, ethyl or phenyl; alkoxy groups containing from 1 to about 4 carbon atoms; or one substituent selected from each of these groups. Alternatively, one of the R" substituents can be a monovalent fluorinated hydrocarbon radical containing from 3 to 20 carbon atoms, such as 3,3,3-trifluoropropyl.

As used herein to define the substituents represented by R, R', R", and R"", the term "monovalent hydrocarbon radical" includes hydrocarbon radicals containing from one up to twenty or more carbon atoms. These radicals can be alkyl such as methyl, ethyl, n-propyl, iso-propyl, butyl, decyl and dodecyl; cycloalkyl such as cyclohexyl, aryl such as phenyl and naphthyl, alkaryl such as tolyl or aralkyl such as benzyl.

When a monovalent hydrocarbon radical is alkyl it preferably contains from 1 to about 10 carbon atoms, most preferably from 1 to 4 carbon atoms. The preference for certain hydrocarbon radicals as substituents on the present silanes is based on the availability of the intermediates used to prepare the reactants containing these substituents. For the same reason cyclohexyl is the preferred cycloalkyl radical, phenyl is the preferred aryl radical and in those instances when one of the substituents represented by R" is a fluoroalkyl radical, it is preferably 3,3,3-trifluoropropyl.

The divalent hydrocarbon radical represented by R"' can contain from 3 to 6 atoms. R"' can be a linear alkylene radical such as 1,3-propylene, 1,4-butylene, or 1,6-hexylene, or a branched alkyene radical such as 2-methyl-1,3-propylene.

Representative ketoximes that are reacted with silanes in accordance with the present method include
acetone ketoxime
methylethyl ketoxime
diethyl ketoxime
phenylethyl ketoxime
diphenyl ketoxime
benzophenone ketoxime
methylisopropyl ketoxime
methylisobutyl ketoxime and
cyclohexylmethyl ketoxime Because the present ketoximosilanes will undergo hydrolysis in the presence of even trace amounts of moisture these compounds should be prepared and stored under anhydrous conditions. The reactions used to prepare the compounds are preferably conducted under an inert atmosphere such as nitrogen.

The following example describes a preferred embodiment of the present method and should not be interpreted as limiting the scope of the accompanying claims. All parts and percentages in the example are by weight unless otherwise indicated.

EXAMPLE 1

A glass reactor equipped with a magnetically activated stirrer was purged with dry nitrogen and then charged with 143 grams (1 mole) of a silane corresponding to the formula

(CH$_3$)$_2$SiCH$_2$CH(CH$_3$)CH$_2$NMe.   (III)

The reactor was then sealed using a rubber septum. A 90 gram (1 mole) quantity of methylethylketoxime was then added to the reactor by injecting it through the rubber septum. The resultant mixture was then heated until the temperature of the mixture reached 70 degrees C.

The infra-red absorption spectrum of the resultant reaction product did not exhibit the strong, broad absorption at 3250 cm$^{-1}$ that is characteristic of the =NOH group. A strong absorption at 910 cm$^{-1}$ and a weaker absorption characteristic of the =NH group were present in the spectrum of the reaction product but not in either of the starting materials. In addition, a strong absorption characteristic of the silane represented by formula III was absent in the reaction product.

The nuclear magnetic resonance spectrum of the reaction product showed the following absorptions, reported in ppm downfield from tetramethylsilane: a singlet at 0.11 ppm, corresponding to the six hydrogens present in the two silicon bonded methyl radicals; complex absorptions within the range from 0.2 to 1.0 ppm, which were assigned to hydrogen atoms present in the SiCH$_2$CH(CH$_3$), CH$_3$CC=N and CCH$_2$N groups; an absorption at 1.73 ppm assigned to N=CCH$_3$; and complex absorptions within the range from 1.8 to 2.4 ppm, assigned to —NCH$_3$, CCH$_2$C=N, and CCH$_2$N. The spectrum was similar to one obtained for tris(methylethylketoximo)methylsilane.

These data indicate that the initial reactants had been consumed to form a compound of this invention represented by the formula (MeEtC=NO)(Me)$_2$SiCH$_2$CH(Me)CH$_2$N(H)Me where Me represents methyl and Et represents ethyl.

That which is claimed is:

1. A method for preparing an organosilane represented by the formula (RR'C=NO)R"$_2$SiR"'NR""H, where R and R' represent identical or different monovalent hydrocarbon radicals, the two R" substituents individually represent a monovalent hydrocarbon radical, a monovalent fluorinated hydrocarbon radical or an alkoxy group, R"' represents an alkylene radical containing from 3 to 6 carbon atoms, and R"" represents a monovalent hydrocarbon radical or a hydrogen atom, said method comprising the steps of
(1) reacting under a substantially anhydrous, inert atmosphere and at a temperature of from 30 to 100 degrees C. a ketoxime of the formula RR'C=NOH and an organosilicon compound of the formula

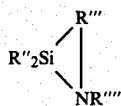

for a sufficient time to form said organosilane, and (2) isolating said organosilane from the reaction mixture.

2. A method according to claim 1 where said monovalent hydrocarbon radicals represented by R, R', and R'''' are, individually, alkyl containing from 1 to 20 carbon atoms, cycloalkyl, or aryl and R'' represents alkyl containing from 1 to 20 carbon atoms or fluoroalkyl containing from 3 to 20 carbon atoms.

3. A method according to claim 2 where said alkyl radical contain from 1 to 4 carbon atoms, said cycloalkyl radical is cyclohexyl, said aryl radical is phenyl, said fluoroalkyl radical is 3,3,3-trifluoropropyl and any alkoxy radicals represented by R'' are methoxy.

4. A method according to claim 3 where R, R''' and at least one of the substituents represented by R'' are methyl, any remaining R'' substituents are methoxy, R' is ethyl and said alkylene radical is propylene or —$CH_2CH(CH)_3CH_2$—.

* * * * *